United States Patent [19]

Akamatsu et al.

[11] Patent Number: 4,550,735
[45] Date of Patent: Nov. 5, 1985

[54] ELECTRODE FOR AN ELECTROCARDIOGRAPH

[76] Inventors: Norio Akamatsu, 1-8, Higashiyoshinocho 2-Chome, Tokushima-shi, Tokushima, Japan, 770; Yasuhiro Toyosu, 15-5, Minamikomatsushimacho, Komatsushima-shi, Tokushima, Japan, 773

[21] Appl. No.: 531,643

[22] Filed: Sep. 13, 1983

Related U.S. Application Data

[63] Continuation-in-part of Ser. No. 405,955, Jul. 29, 1982, Pat. No. 4,517,983.

[51] Int. Cl.[4] .............................................. A61B 5/04
[52] U.S. Cl. ...................................... 128/639; 128/696
[58] Field of Search .............. 128/639, 642, 643, 644, 128/695, 696, 731, 732, 734, 733, 741, 744, 683–685, 799, 795, 796, 802, 329 A, 303.18

[56] References Cited

U.S. PATENT DOCUMENTS

| | | | |
|---|---|---|---|
| 3,323,515 | 6/1967 | Foner et al. ........................ | 128/712 |
| 3,534,733 | 10/1970 | Phipps et al. ...................... | 128/643 |
| 3,628,527 | 12/1971 | West ................................... | 128/639 |
| 3,971,364 | 7/1976 | Fletcher et al. .................... | 128/695 |
| 4,016,886 | 4/1977 | Doss et al. ......................... | 128/784 |
| 4,037,590 | 7/1977 | Dohring ............................. | 128/790 |
| 4,121,575 | 10/1978 | Mills et al. ......................... | 128/644 |
| 4,275,743 | 6/1981 | Hjort ................................... | 128/644 |

*Primary Examiner*—William E. Kamm
*Attorney, Agent, or Firm*—Wenderoth, Lind & Ponack

[57] ABSTRACT

An electrode for an electrocardiograph used for measuring potentials of a number of points of a body surface near the heart and producing an isopotential map thereof, has a plurality of spring-loaded rods movably mounted for reciprocal movement in the direction of the lengths thereof and urged toward the human body surface, and a pin contact set on the one end of each rod. Each pin contact set has a plurality of parallel electrically conductive spring-loaded pin contacts, movably mounted for movement reciprocally in the direction of its length for directly contacting the human body surface. The pin contacts of each set are mounted in a small area close to one another and are mutually electrically connected in parallel, the space between the pin contacts of each pin contact set being much smaller than the space between the adjacent small areas of the pin contact sets, whereby the potential at a position on the body surface contacted by a pin contact set can be detected as long as one pin contact in the set is in good contact with the body, even if the other pin contacts in the set are in bad contact.

6 Claims, 14 Drawing Figures

FIG. I

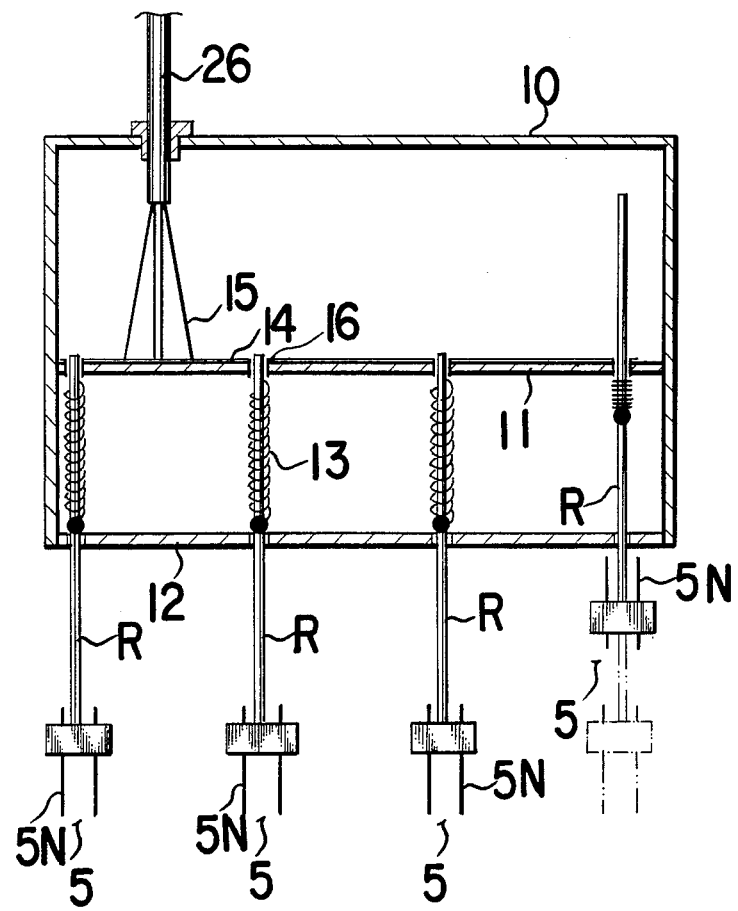

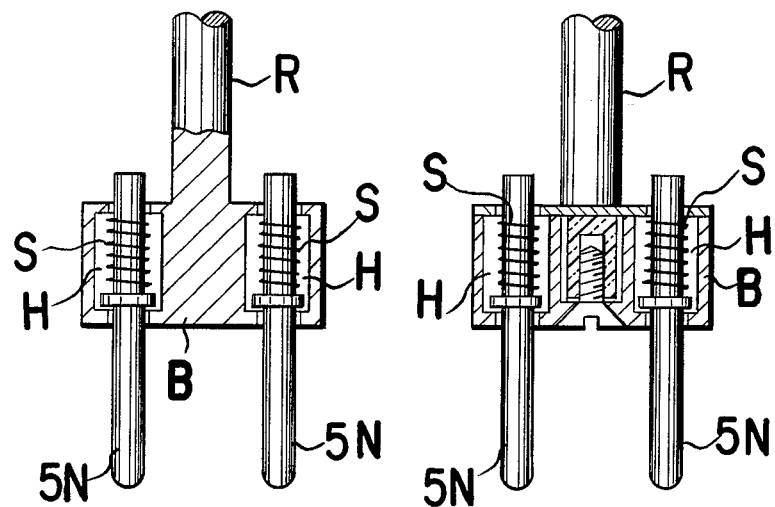

ELECTRODE FOR AN ELECTROCARDIOGRAPH

This Application is a continuation-in-part of Application Ser. No. 405,955, filed July 29, 1982, now U.S. Pat. No. 4,517,983.

FIELD OF THE ART

The present invention relates to an electrode for an electrocardiograph used for measuring the potentials of a number of points of the human body surface near the heart, and through information processing of the measured of the potentials, the electrical activity of the heart can be judged.

BACKGROUND OF THE INVENTION

Accordingly to a generally used electrocardiograph, the potential change of a six points on the chest over a period of time is measured and represented on a graph with time as the abscissa and the potential as the ordinate, whereby the heart disorder is detected from the wave form obtained relative to each point. According to a recently developed electrocardiograph, 80 to 200 electrodes are applied to various points of the body surface near the heart and the potential of each point is measured, whereby the electrical activity of the heart ca be judged. By this electrocardiograph, an isopotential map for a certain time is made for the body surface near the heart, as shown in FIG. 1. In this isopotential map, the body surface potentials are shown on isopotential lines so as to make it possible to examine the distribution of the body surface potentials. This isopotential map is obtained e.g. by temporarily storing the potential of each electrode in a memory unit, calculating the isopotential points based on the potential of each electrode through a computer, and then drawing the isopotential lines e.g. at a pitch of a few tens of microvolts on a television or an XY-plotter.

When using this electrocardiograph, a plurality of isopotential maps are obtained at intervals of the sampling time and the enlargement or contraction of the positively and negatively charged parts of the body surface near the hear can be recognized from the change of the potential gradient, whereby the electrical activity of the heart is indicated.

However, in the electrocardiograph of this kind, it is difficult to apply a number of electrodes to the points of the body surface with small contact resistance, and to stably and correctly detect the potential of each point.

For example, it takes four persons as long as 30 minutes to 1 hour to correctly place the conventional suction type electrodes at about 100 points of the body surface, and only one or two patients can be examined in a hour even under the best conditions.

It is necessary that the electrodes of an electrocardiograph be applicable to any person, adult or child, male or female, having different body shapes. The electrodes must be free from errors in potential measurement due to the unevenness of the body surface or its upward and downward motion caused by the breathing. Further, the electrodes are required not to cause any terror, pain or sense of oppression to patients. Further, they must be able to be applied or removed easily and rapidly, and to be easily maintained. Furthermore, it is necessary to place the electrodes correctly relative to one another and without deviation.

In detecting the potentials of points on the body surface preferably all the electrodes are pressed onto the body surface with a strong force so as to stably and correctly measure the potentials at the electrode contact points. However, in an electrocardiograph for detecting the potentials of many points on the human body, a number of electrodes are employed. And if the pressure applied for an electrode is 500 g and 100 electrodes are used, a force as strong as 50 kg is applied to the body in the area where the electrodes are applied, e.g. the chest. This necessarily gives a strong sense of oppression to the patients. Therefore, such an electrocardiograph is extremely unsuitable for examining the heart of patients having reduced strength.

Consequently, practically usuable electrodes cannot be obtained simply by increasing the force with which the electrodes are pressed onto the body.

In a conventional electrocardiograph, since signals fed from each electrodeare amplified and shown, in a graph, the bad contact of electrodes can be easily recognized from the graph for the particular electrode.

However, in the improved electrocardiograph described above, an isopotential map of the body surface at the time of measurement is shown, and therefore, it is more difficult than in the conventional electrocardiograph to judge from the map whether there is bad contact of electrodes. Consequently, in order to examine the heart with a high accuracy, all the electrodes must always be in sure electrical contact with the body surface. If a conventional suction type electrode or an adhesive tape type electrode makes bad electrical contact for one second per 100 seconds, on the average on of the 100 electrodes is always in bad contact and accurate measurement cannot be performed.

It is known that an electrocardiogrph which produces an isopotential map of the body surface near the heart can indicate more accurately the electrical activity of the heart than a conventional electrocardiograph which shows only the change of the voltage of the measuring point. However, with such an electrocardiograph, potentials of a large number of points on the body surface must be detected simultaneously and accurately. Since this problem has not yet been sufficiently overcome, the electrocardiograph of this type has not yet come into widespread use.

OBJECTS AND BRIEF SUMMARY OF THE INVENTION

An object of the present invention is to provide an electrode for an electrocardiograph by which the potentials of a number of points of the body surface can be stably, surely and accurately detected and the electrical activity of patients with different body shapes can be measured in a short time.

Another object of the present invention is to provide an electrode for an electrocardiograph, in which even if one of the needle electrodes fals to be in sure contact with the body surface, an accurate potential distribution map can nevertheless be obtained.

A further object of the present invention is to provide an electrode for an electrocardiograph, in which the force with which the needle electrode is applied to the body surface can be decreased and potential distribution map of the body surface can be obtained without giving heavy pain and discomfort to patients.

The above and other objects and novel features can be more readily recognized from the following explanation and the appended drawings. These drawings are only for explanation and do not limit the scope of the present invention.

BRIEF DESCRIPTION OF THE DRAWINGS

FIG. 4 is a sectional view of an example of electrode; FIGS. 5 and 6 are enlarged sectional views of the lower end of an electrode rod showing the pin contacts; FIG. 7 is a bottom view of the end of a rod.

EXAMPLE OF THE INVENTION

Figure 1:
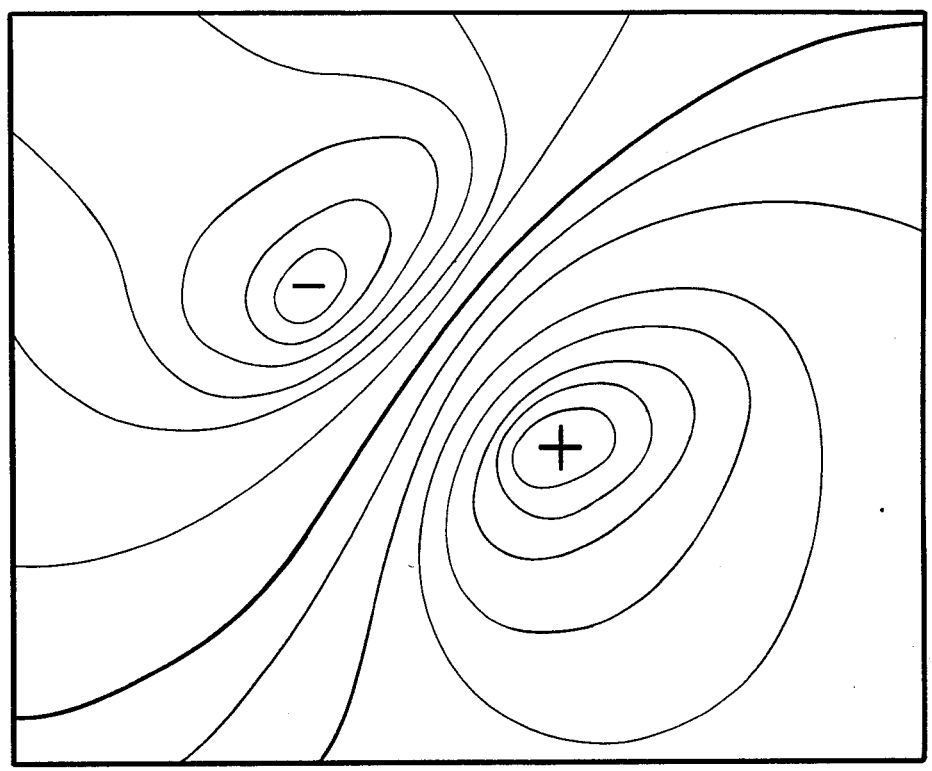
FIG. 1 is an isopotential map of the body surface near the heart.
Figure 2:
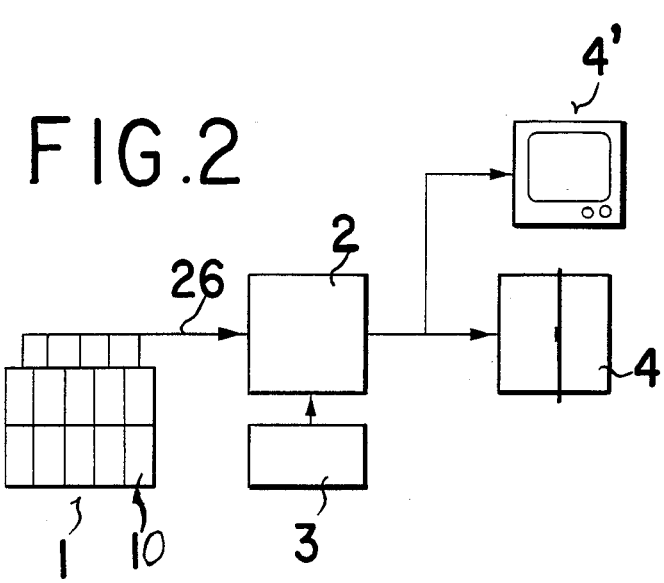
FIG. 2 is a block diagram of an example of an electrocardiograph in which an electrode according to the present invention can be used.

An electrocardiograph as shown in FIG. 2 comprises an electrode means 1, an electronic processing circuit 2, an operating switch 3, aXY-plotter 4 and a monitor 4'.

Figure 3:
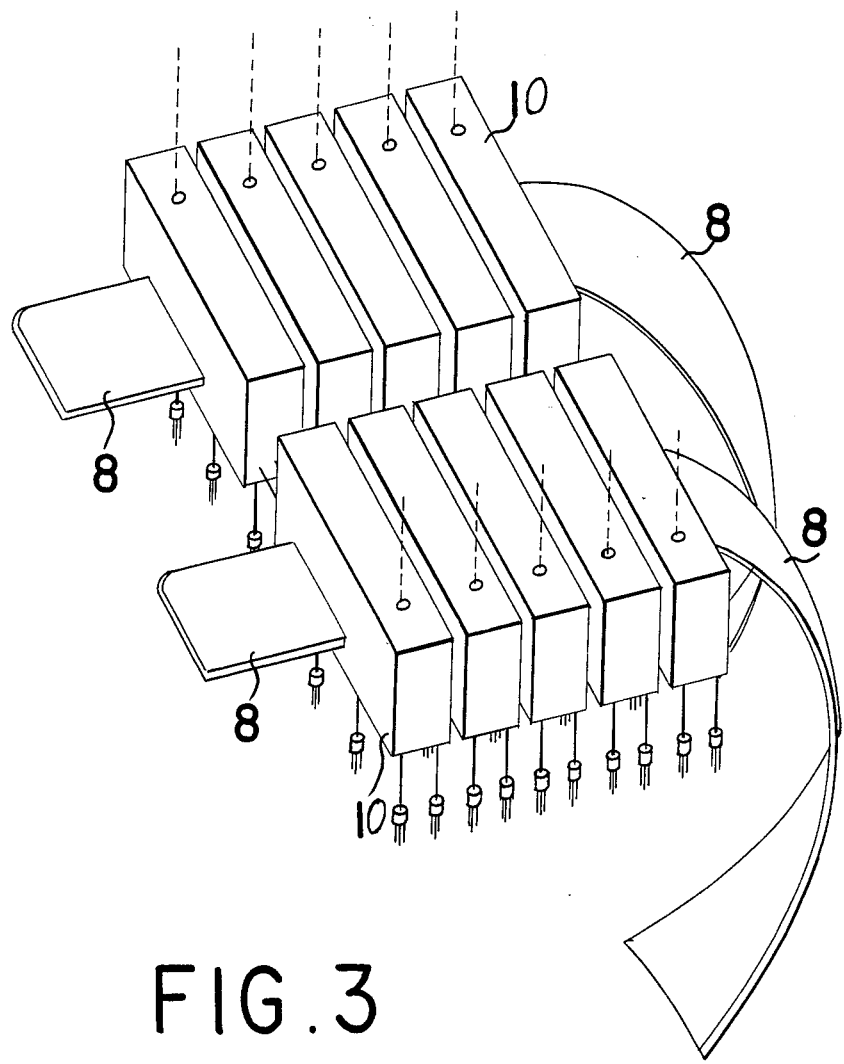
FIG. 3 is a perspective view of an example of electrode.
Figure 8:
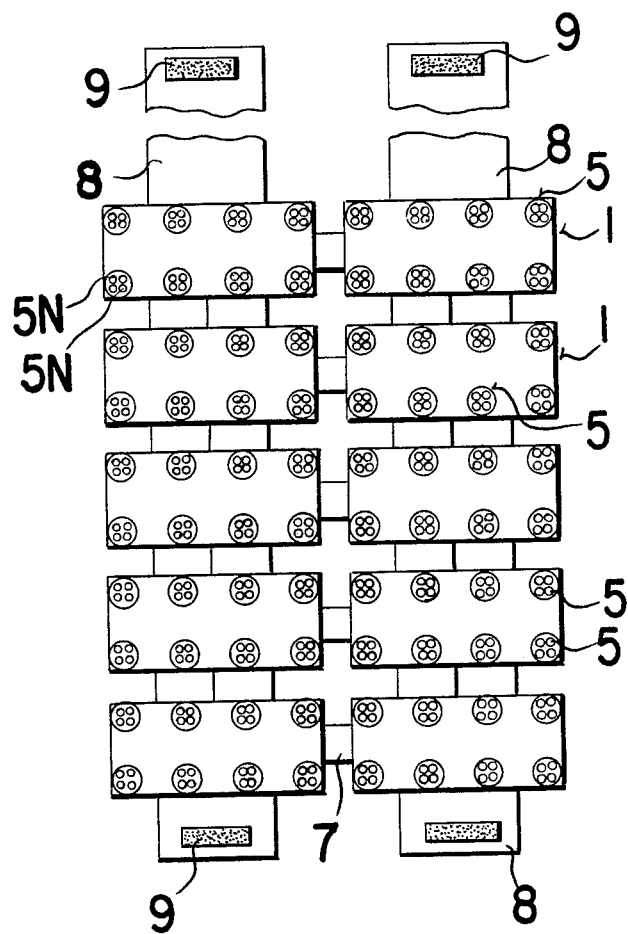
FIG. 8 is a bottom view of an example of electrode as shown in FIG. 3.

As shown in FIGS. 3, 4 and 8, the electrode means 1 comprises ten electrode housings 10 each containing eight sets 5 of needle electrodes or pin contacts 5N.

The electrode housings 10 are mutually connected by a movable member 7 in the form of a string-like rubber-like elastic member. An elastic band 8 is connected to the outermost electrode housings 1, and a connecting tape 9 is saved onto the leading edge of the band 8.

As shown in FIGS. 4 and 5, the electrode housings provided with the rods R which are arranged to be movable in the axial direction.

Each electrode housing 10 comprises a downwardly opened box-like case constituting an electrode body, and two electrically isolated plate members 11 and 12. The rods R extend through the plate members 11 and 12 so as to be movable inward and outward therethrough. Coil springs 13, constituting push members, are provided between the plate members 11 and 12 with each of the rod R extending through a coil spring 13.

Means other than a coil spring can be used for the push member for the rod R. For example, an air or oil cylinder can be used for the push member.

The coil spring 13 is a counter spring and its lower end is connected to the middle portion of the rod R and its upper end extends through the plate member 11 and is connected to a conductor printed on the upper surface of the plate member 11.

Each of the electrode housings 1 shown in FIGS. 3 and 8 is provided with eight pin contact sets 5, the total number of pin contact sets preferably being from 80 to 200, and each pin contact set 5 is here shown as having four pin contacts 5N. The pin contact sets preferably have from two to six pin contacts.

Four pin contacts 5N are arranged close to one another. The space between the pin contacts 5N is much smaller than that between the pin contact sets 5. For example, the former is several to several tens of fractions of the latter. Each pin contact is a metal wire of stainless steel, copper, aluminium or conductive alloy.

As shown in FIG. 5, each pin contact 5N is inserted into an axially elongated through hole H provided in a base B on the head of a rod R so as to be movable in parallel with the rod R. The middle portion of the pin contact 5N is provided with a coller within the through hole H. The opening of the axially elongated through hole H is somewhat reduced in size. And a coil spring S provided in the through hole H. The coil spring S is a resilient member for resiliently urging the pin contact outwardly, and it is a counter spring acting on the pin contact 5N. The lower end of the coil spring S engages the collar of the needle electrode 5N and the upper end of thereof is engages around the reduced size opening of the axially elongated through hole H. The coil spring S has electric conductivity and the upper and lower ends thereof are in electrical contact with the pin contact 5N and the base B by means of their own resiliency or by being welded or soldered onto the pin contact 5N and the base B of the rod R, so that the heart potential is transmitted from the pin contact 5N to the rod R.

In FIG. 6, the pin contacts 5N extend through the nonconductive base B. The base B is formed of nonconductive material such as synthetic resin and fixed onto the head of the rod.

As shown in FIG. 7, the base B is provided with axially elongated through holes H with a given space therebetween similarly to the base B in FIG. 5, and the pin contacts extend through the axially elongated through holes H. The upper end of the coil spring S in the axially elongated through hole is electrically connected to the collar of the rod R.

With this construction, if the lower end face of the base B comes in contact with the body surface, the contact area does not increase to more than the contact area when only the needle electrode is in contact with the body surface, so that a set of pin contacts can accurately detect the potentials of the points of the body surface with a small contact area.

If any one of the pin contacts 5N of a set 5 is out of contact with the body surface, the potential of the body surface can be detected through another pin contact 5N of the sets which is in contact with the body surface. Consequently, by an electrocardiograph having electrodes of such a structure, the accurate and sure detection of the potential of the body surface is ensured.

If an electrode set comprises four pin contacts 5N and one pin contact makes bad contact for 1 second per 100 seconds, the probability of all of the four pin contacts being in bad contact at the same time is 1 second per 100,000,000 seconds, i.e. close to substantially zero.

The space between the pin contacts 5N is from 1 mm to 15 mm.

In the upper plate member 11 of FIG. 4, a tube member 16 is inserted into each through hole through which a rod R extends.

Figure 9:
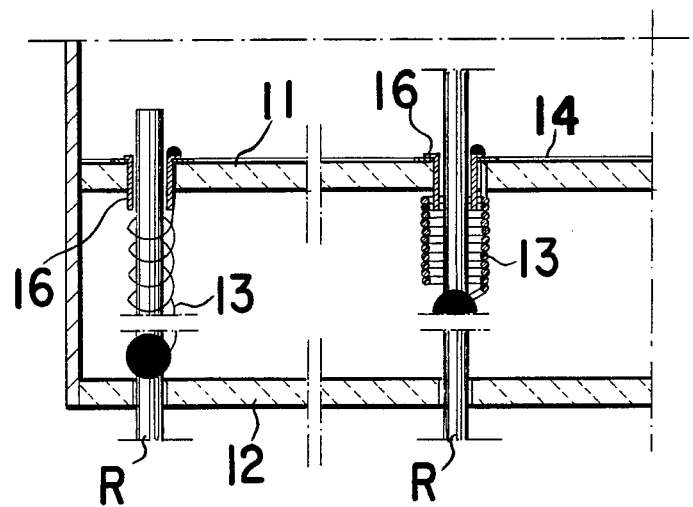
FIG. 9 is a broken sectional view on an enlarged scale illustrating a part of the electrode of FIG. 4.
Figure 10:
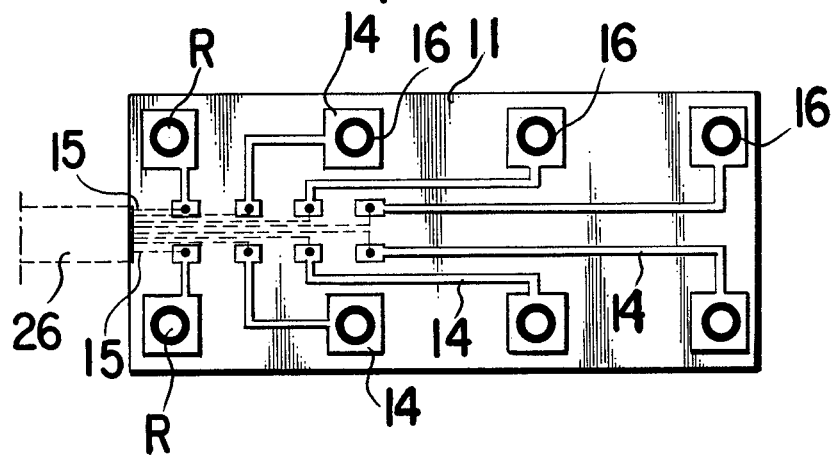
FIG. 10 is a plan view of a plate member forming part of the electrode of FIG. 4.

The tube member 16 comprises a metal tube or a tube with an inside surface which is smooth and has low friction resistance, in order to lower the friction resistance between the tube member 16 and the rod R which is stainless steel, copper, aluminium or conductive alloy. As shown in FIG. 9, the tube member 16 extends downwardly somewhat below the lower surface of the plate member 11. The upper end of the coil spring 13 is connected to the lower end of the tube member 16 and the rod R is pushed upwardly through the tube member and the coil spring is compressed. According to this structure, when the rod R is pushed to the uppermost position, the pressed coil spring 13 is prevented from coming into contact with the rod R and thus from restricting the movement of the rod R. Therefore, the rod R can always move smoothly through the tube member. The rod R being pushed out by means of the coil spring 13 is prevented from coming out of the plate 12 by an enlarged portion on the rod R, to wich the lower end of the coil spring 13 is fixed by slder or welding, and which it too large to fit through the through hole 17 in the lower plate member 12. As shown in FIG. 10, the conductors 14 of copper or the like are printed on the upper surface of the upper plate member 11 and the lead wires 15 are connected to one end of the conductors 14.

Figure 11:
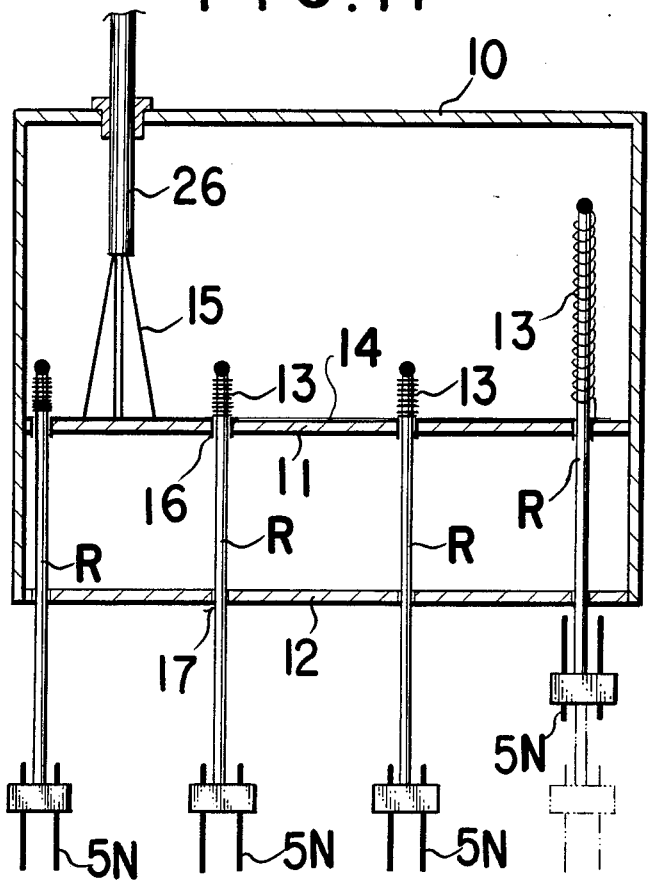
FIGS. 11 and 12 are sectional views of further examples of the electrode.

In the electrode housing shown in FIG. 11 the coil springs 13 are provided on the upper end portions of the rods R and above the upper plate member 11. And the rods R extend through the coil spring 13. Each coil spring is a tension spring. The upper end of the coil spring 13 is connected to the upper end of the corresponding rod R and the lower end is connected to the corresponding conductor printed on the surface of the plate member 11. The lead wires 15 are connected to the respective conductors 14.

Figure 12:
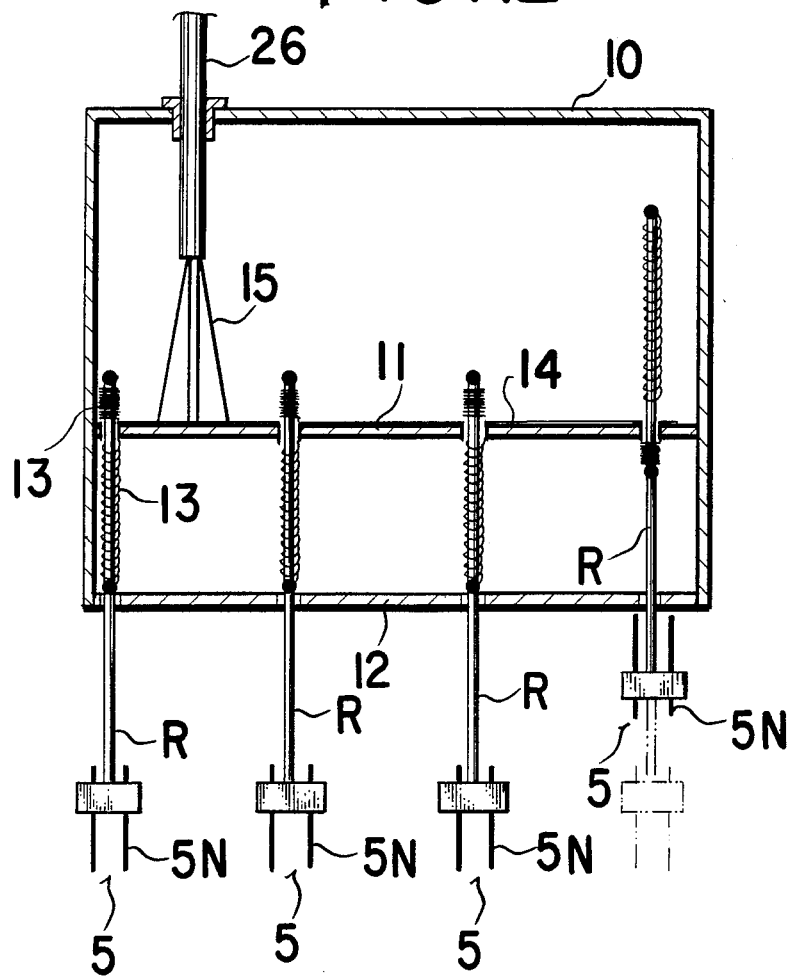

In the electrode housing shown in FIG. 12, coil springs 13 are provided above and below the upper plate member 11. According to this structure, one end of either one or both of the upper and lower coil springs is connected to the corresponding conductor 14 on the plate member 11, and the lead wires 15 are connected to the respective conductors 14. In this case, either of the coil springs may be soft, that is, have a relatively low damping factor which indicates the power required for stretching the coil spring per a unit length.

The coefficients of resiliency of the coil springs 13 for urging the rods R and the coil springs S for urging the pin contacts 5N are preferably so determined that the rods R are completely pushed in when four pin contacts 5N are completely pushed into the axially elongated through holes.

The movable member 7 connecting the electrode housings with one another may be formed of nonelastic string or belting, or soft and elastic string or belting.

The lead wires 15 connected to the electrodes are gathered into an electrically shielded wire 26 and connected to the electronic circuit 2.

Since the potentials detected by the electrodes are rather low, attention must be paid to shielding from external noises.

For this purpose, a metal electrode case shield is provided whereby the ratio of signal to noise can be improved. In order to further lower the noise level, it is preferable that a device for amplifying the detected signal from the electrode, e.g. an operating amplifier is provided within the electrode housing.

Most preferably, the amplifier 18 is one having high input impedence of FET input. Such an amplifier is not necessarily voltage-amplified, and amplifiers of high input impedance, low output impedance and voltage gain 1 can be used. Naturally, an amplifier can be used the gain of which is above one.

If the rod R is a big round tube, the amplifier can be mounted in the rod R, or the amplifier can be mounted in the base B too. The amplifier is shielded by the electrically conductive electrode case 10 or rod R or base B in which the amplifier is mounted.

Figures 13, 14:
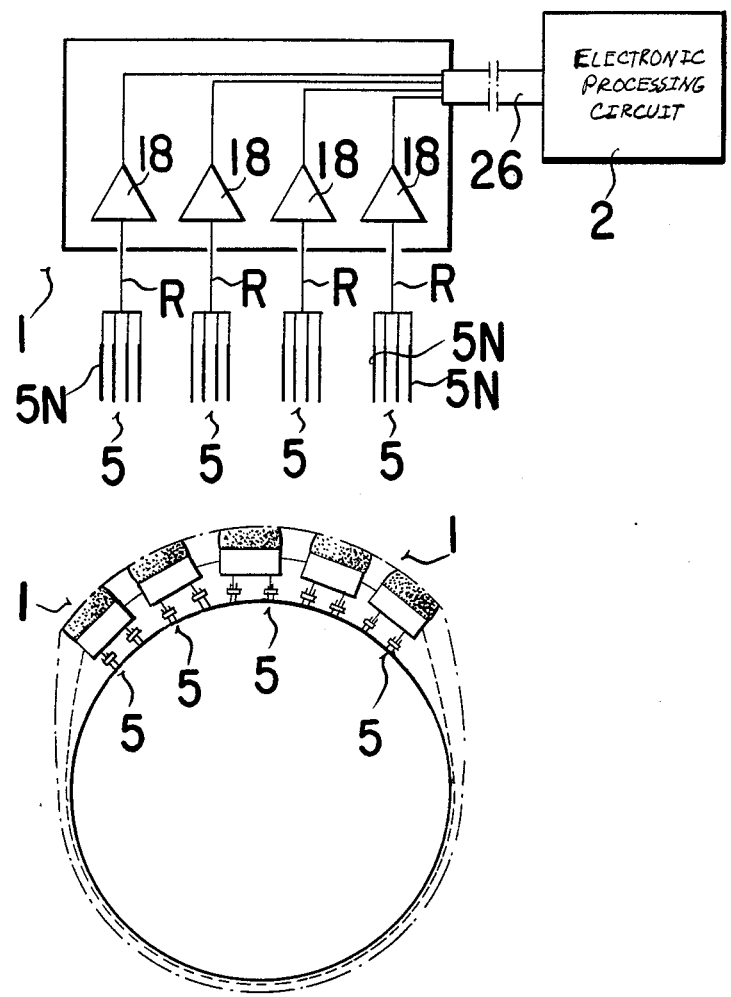
FIG. 13 is a circuit diagram of an amplifier which is connected to the rods.
FIG. 14 is a sectional view illustration the application of the electrodes to the body surface.

In FIG. 14, the electrodes are shown applied to the human chest surface, each electrode being put on the body surface near the heart, and then the two ends of the winding band 8 are connected mutually by a connectable tape 9 whereby the electrodes are applied to the body surface under a given pressure. In this step, the outside of the electrode housing 1 may be further secured by an elastic band 19 so as to push the electrodes more intensely The electronic circuit 2 is adapted to perform information processing of the electrical signals transmitted through the electrodes according to a known system, for example, to calculate the isopotential curves based on the electrical signals transmitted from the electrodes at intervals of a sampling time, and then transmit the output signals therefrom to the X-Y plotter 4 and the monitor 4' to show the isopotential maps of the body surface.

An electrode means according to the present invention can be in an electrocardiograph as shown in FIG. 2 and can stably detect the heart potentials. The electrode means can be used in a conventional electrocardiograph in which potentials of a plurality of human body surface points near the heart are detected to detect the change of the heart potential in a given period of time.

INDUSTRIAL AVAILABILITY

An electrode means for an electrocardiograph according to this invention is useful as an apparatus for detecting heart disease or detecting heart desease accompanied by other diseases in its early stages. And since, according to this invention, the time required for examining a person is very short, the operation being very easy, and the parts thrown away after a measurement, such as an adhesive tape type electrode, being few and thus the cost of the measurement being low, it is especially suitable for group examination for heart disease.

What is claimed is:

1. An electrode means for an electrocardiograph used for measuring potentials of a number of points of a body surface near the heart and producing an isopotential map thereof, said electrode means comprising:
   a plurality of rods movably mounted for reciprocal movement in the direction of the lengths thereof;
   resilient members, one connected to each rod, for resiliently urging one end of each rod in the direction of its length toward the human body surface;
   a pin contact set on said one end of each rod, each pin contact set having a plurality of parallel pin contacts, each pin contact being conductive at least on its surface and each pin contact being movably mounted for movement reciprocally in the direction of its length for directly contacting the human body surface;
   further resilient members, one connected to each pin contact, for resiliently urging the end of each pin contact in the direction of its length toward the human body surface;
   the pin contacts of each set being mounted in a small area close to one another on said rod and being mutually electrically connected in parallel, the space between the pin contacts of each pin contact set being much smaller than the space between the adjacent small areas of the pin contact sets, whereby the potential at a position on the body surface contacted by a pin contact set can be detected as long as one pin contact in the set is in good contact with the body, even if the other pin contacts in the set are in bad contact.

2. An electrode means as claimed in claim 1 in which each pin contact set comprises from two to six pin contacts.

3. An electrode means as claimed in claim 1 in which each pin contact is a metal pin.

4. An electrode as claimed in claim 1 in which the resilient members and the further resilient members are coil springs.

5. An electrode as claimed in claim 4 in which each rod is a conductive material rod, and the coil springs are conductive material coil springs, the coil spring for each pin contact being coiled around the pin contact and having one end electrically connected to the pin contact and the other ends of the coil springs for the pin contacts of a set being mutually electrically connected in parallel to the rod on which the set is mounted.

6. An electrode as claimed in claim 1 further comprising an electrode case in which said rods are mounted, and a plurality of amplifiers in said electrode case, one connected to the pin contacts in each set.

* * * * *